United States Patent [19]

Sommer et al.

[11] Patent Number: 4,673,745

[45] Date of Patent: Jun. 16, 1987

[54] ISOQUINILINIUM CHEMICAL AGENTS

[75] Inventors: Harold Z. Sommer, Havre de Grace; Omer O. Owens, Abingdon; Jacob I. Miller, Baltimore, all of Md.

[73] Assignee: The United States of America as represented by the Secretary of the Army, Washington, D.C.

[21] Appl. No.: 562,946

[22] Filed: Jun. 29, 1966

[51] Int. Cl.⁴ .......................................... C07D 413/00
[52] U.S. Cl. .................................... 546/147
[58] Field of Search .................. 260/88 A; 167/33 D, 167/46, 47; 546/147

[56] References Cited

PUBLICATIONS

Jones, Jr. et al, *J. Org. Chem.*, 22, 783–6 (1957).

Primary Examiner—Edward A. Miller

Attorney, Agent, or Firm—Anthony T. Lane; Robert P. Gibson; Harold H. Card, Jr.

[57] ABSTRACT

New chemical compounds having the generic formula:

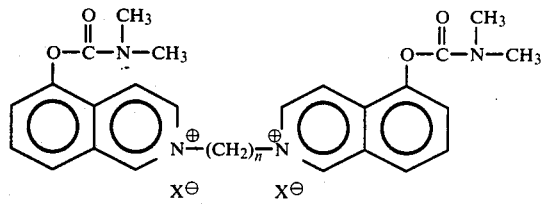

where n is 3 to 16 carbon atoms and where X is one equivalent of a monovalent or polyvalent anion, and having utility as toxic agents.

6 Claims, No Drawings

ISOQUINILINIUM CHEMICAL AGENTS

This invention relates to the synthesis of new toxic chemical compounds which are useful as chemical warfare agents and as physiologically active materials. More particularly, our invention is concerned with novel symmetrical quaternary compounds.

These chemical agents act mostly on the peripheral autonomic cholinergic nervous system which includes the motor nerves, all preganglionic fibers, the postganglionic parasympathetic fibers, the ganglia, and the neuromuscular junctions. The transmission of impulses along a nerve or from nerve fibers to muscle fibers or secretory cells or from one nerve fiber to another across synapses in ganglia is thought to involve chemical changes. Our chemical agents interfere with the normal process of neuromuscular impulse transmission and thus disrupt the propagation of impulses from nerves to muscles. We have also found these compounds to be extremely toxic at relatively low dose levels in various animals.

The object of this invention is to synthesize new lethal agents in high yields wherein said products are well suited for industrial scale manufacture.

Other objects of and uses for the invention will in part be obvious and will in part appear hereinafter in the following detailed description thereof.

Our compounds may be employed in any munition suitable for handling a solid toxic agent such as bombs, shells, spray tanks, rockets, aerosol generators, and others. If a liquid agent is desired, our compounds can be dissolved in polar solvents such as water, lower alcohols, chloroform, and acetonitrile.

In accordance with our invention, a mixture of hydroxyisoquinoline and a dialkylcarbamyl halide were heated on a steam bath. The mixture was cooled and the semi-solid was triturated with a hydrocarbon solvent. The material was dissolved in water and then made basic. The solution was extracted several times with chloroform solvent, the extracts were combined and dried over an anhydrous metal salt such as magnesium sulfate. The solvent was evaporated and the solid residue was recrystallized from a hydrocarbon solvent. The solid residue was quaternized with an α,ω-dihaloalkane in the presence of a polar solvent. This solution was refluxed for several hours. On cooling, a precipitate was formed, filtered, and recrystallized from a polar solvent. The product was then dried in vacuo at room temperature.

The new compounds of our invention may be represented by the following generic formula:

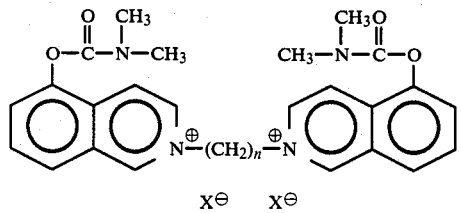

where n is 3 to 16 carbon atoms and where $X^{\ominus}$ is one equivalent of a monovalent or polyvalent anion.

The procedure used for the preparation of the new toxic materials is schematically shown as follows:

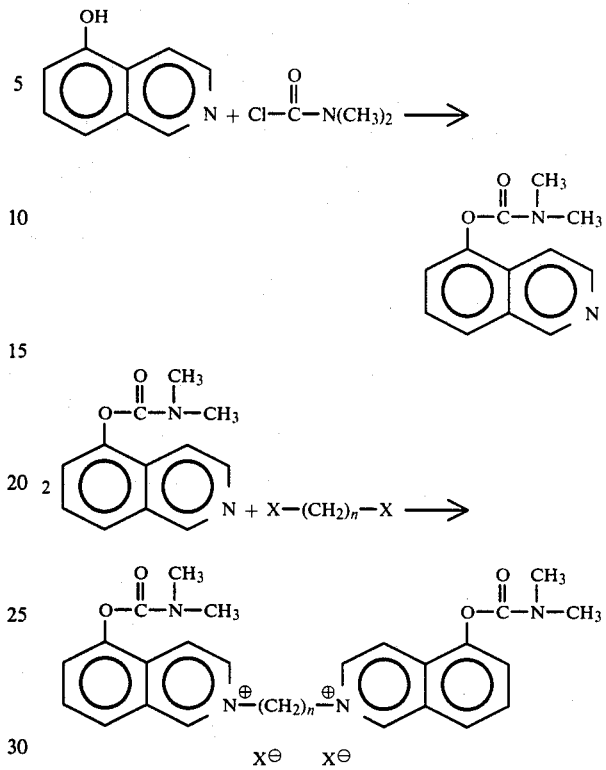

where n is the same as above, X is a halide radical and $X^-$ is the corresponding halide anion, preferably chlorine, bromine, or iodine, that is, the halogens having an atomic weight of 35.5 to 127.

If compounds are desired in which X is other than a halide ion, the above quaternary compounds are treated with the desired acid by a simple exchange reaction as set forth below:

EXAMPLE

Synthesis of octamethylene-bis(5-dimethylcarbamoxy-isoquinolinium bromide)

A mixture of 5-hydroxyisoquinoline (2.0 g.) and dimethylcarbamyl chloride (4.0 ml.) was heated on a steam bath for two hours. The mixture was cooled and the formed semi-solid mass was triturated with benzene. The resulting solid was dissolved in water and the solution made basic with IN sodium hydroxide. The solution was then extracted with three portions of chloroform, the extracts were combined and dried over anhydrous magnesium sulfate. The solvent was evaporated and the solid residue was recrystallized from petroleum ether. The pure crystalline product, 5-dimethylcarbamoxyisoquinoline, (2.0 g.) was then mixed with 1,8-dibromooctane (1.25 g.) in 6 ml. of acetonitrile and refluxed for 8 hours. On cooling, a precipitate was formed, filtered, and recrystallized from acetonitrile. After drying in vacuo for 14 hours at room temperature, the product (2.8 g.) contained 3.5% of water, and melted at 121°–125° with decomposition.

Anal. Calc. for $C_{32}H_{40}Br_2N_4O_4 3.5\%H_2O$ C, 52.8; H, 5.8; Br, 21.9; O, 11.7 Found: C, 53.1; H, 6.0; Br, 21.5; O, 11.7

| Toxicity Intravenus LD$_{50}$ mg./kg. ||
|---|---|
| Mice | Rabbits |
| 0.016 | 0.006 |

The compounds which are described above are representative of our invention and are listed below by name.

Trimethylene-bis(5-dimethylcarbamoxyisoquinolinium bromide).
Tetramethylene-bis(5-dimethylcarbamoxyisoquinolinium bromide).
Pentamethylene-bis(5-dimethylcarbamoxyisoquinolinium bromide).
Hexamethylene-bis(5-dimethylcarbamoxyisoquinolinium bromide).
Heptamethylene-bis(5-dimethylcarbamoxyisoquinolinium bromide).
Octamethylene-bis(5-dimethylcarbamoxyisoquinolinium bromide).
Nonamethylene-bis(5-dimethylcarbamoxyisoquinolinium bromide).
Decamethylene-bis(5-dimethylcarbamoxyisoquinolinium bromide).
Undecamethylene-bis(5-dimethylcarbamoxyisoquinolinium bromide).
Dodecamethylene-bis(5-dimethylcarbamoxyisoquinolinium bromide).
Tridecamethylene-bis(5-dimethylcarbamoxyisoquinolinium bromide).
Tetradecamethylene-bis(5-dimethylcarbamoxyisoquinolinium bromide).
Pentadecamethylene-bis(5-dimethylcarbamoxyisoquinolinium bromide).
Hexadecamethylene-bis(5-dimethylcarbamoxyisoquinolinium bromide).

We have shown a preferred compound in which the anion is limited to the halogen moiety, in particular the bromide, since the bromoalkanes are readily available and are good quaternizing agents. In general, however, it is only necessary that the anions merely have to meet the requirement of being capable of forming a stable salt with the quaternary nitrogen. Thus, the halogen ions can be exchanged with other anions of a relatively strong monovalent or polyvalent acid by conventional methods. For example, if X is a bromide in the final product, a solution of the compound can be treated with a basic ion exchange resin or mixed with silver oxide and subsequently the desired acid is added to the quaternary hydroxide solution. Anions other than the halogens may be supplied directly or by metathesis with the halide form of the quaternary ammonium compound. Also, suitable as representations of $X^\ominus$ are the anions hydrogen sulfate, nitrate, hydrogen oxalate, perchlorate, and tetraphenylboronate. Representative examples of these additional monovalent or polyvalent end products are:

Decamethylene-bis(5-dimethylcarbamoxyisoquinolinium hydrogen sulfate).
Decamethylene-bis(5-dimethylcarbamoxyisoquinolinium nitrate).
Decamethylene-bis(5-dimethylcarbamoxyisoquinolinium hydrogen oxalate).
Decamethylene-bis(5-dimethylcarbamoxyisoquinolinium perchlorate).
Decamethylene-bis(5-dimethylcarbamoxyisoquinolinium tetraphenylboronate).

We claim:

1. New chemical toxic agents, the compounds having the formula:

$$\text{Structure: two 5-(dimethylcarbamoxy)isoquinolinium groups linked at position by } -(CH_2)_n- \text{ bridge, with two } X^\ominus \text{ counterions}$$

where n is 3 to 16 carbon atoms and where X is one equivalent of a monovalent or polyvalent anion selected from the group of anions consisting of halide, hydrogen sulfate, hydrogen oxalate, nitrate, perchlorate, and tetraphenylboronate.

2. The compound Octamethylene-bis(5-dimethylcarbamoxyisoquinolinium bromide).

3. The compound Nonamethylene-bis(5-dimethylcarbamoxyisoquinolinium bromide).

4. The compound Decamethylene-bis(5-dimethylcarbamoxyisoquinolinium bromide).

5. The compound Undecamethylene-bis(5-dimethylcarbamoxyisoquinolinium bromide).

6. The compound Dodecamethylene-bis(5-dimethylcarbamoxyisoquinolinium bromide).

* * * * *